United States Patent [19]

Inada et al.

[11] Patent Number: 5,337,138

[45] Date of Patent: Aug. 9, 1994

[54] PACKAGE READYING AND INSPECTION APPARATUS

[75] Inventors: Kenichi Inada; Akihiko Takeshita, both of Ohtsu; Tetsuji Masai, Kusatsu, all of Japan

[73] Assignee: Murata Kikai Kabushiki Kaisha, Kyoto, Japan

[21] Appl. No.: 68,080

[22] Filed: May 28, 1993

Related U.S. Application Data

[62] Division of Ser. No. 862,196, Apr. 2, 1992.

[30] Foreign Application Priority Data

Apr. 9, 1991 [JP] Japan .................................. 3-31643[U]
Jun. 28, 1991 [JP] Japan .................................. 3-58567[U]

[51] Int. Cl.⁵ .............................................. G01N 21/88
[52] U.S. Cl. ......................................... 356/36; 356/238
[58] Field of Search ........................... 356/238, 36, 426

[56] References Cited

U.S. PATENT DOCUMENTS 4,866,289 9/1989 Kawamura et al. ............ 356/238 X
5,125,034 6/1992 Hudson et al. ................. 356/238 X

FOREIGN PATENT DOCUMENTS 3941008 6/1990 Fed. Rep. of Germany ...... 356/238

*Primary Examiner*—Vincent P. McGraw
*Attorney, Agent, or Firm*—Spensley Horn Jubas & Lubitz

[57] ABSTRACT

A package inspecting apparatus comprising a yarn end processing section for exerting suction air on the surfaces of packages while rotating trays on a running passage for trays on which packages are fitted, a package inspecting section in which a plurality of optical type package winding-form inspecting devices are received in a dark room, and a weighing section provided with a weight measuring unit, said sections being arranged in series in said order and integrated.

2 Claims, 10 Drawing Sheets

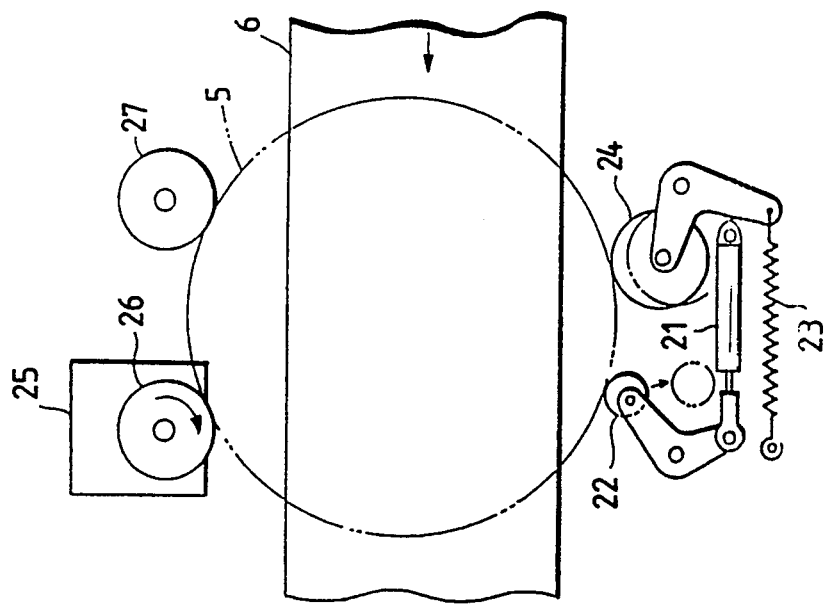
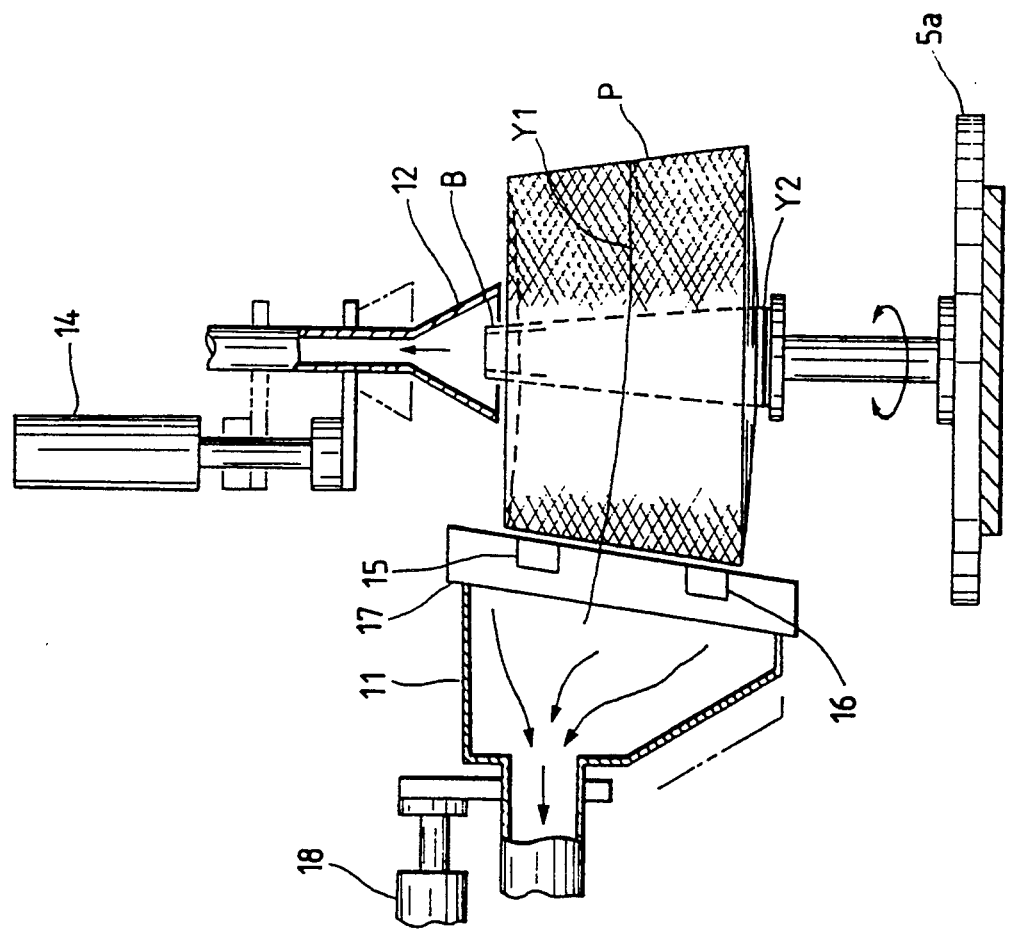

PACKAGE READYING AND INSPECTION APPARATUS

This is a division of application Ser. No. 07/862,196, filed on Apr. 2, 1992.

BACKGROUND OF THE INVENTION

1. Field of the Invention

The present invention relates to a package inspecting apparatus for effectively carrying out yarn end processing, winding-form inspection and weight inspection for packages produced by an automatic winder.

2. Prior Art

Packages produced by an automatic winder are subjected to yarn end processing, winding-form inspection and weight inspection prior to shipment thereof. These inspections often rely upon manual operation, and various apparatuses for automatically carrying out these inspections have been proposed. For example, an apparatus in which winding-form inspecting devices are received in a dark room has been proposed in Japanese Utility Model Laid-Open Publication No. 13965/1988.

However, in the conventional apparatuses, the yarn end processing, winding-form inspection and weight inspection are respectively independent. There was a problem in that a considerable change of the system has to be made in order to incorporate these inspection into and between the automatic winder and the shipment packing line.

Furthermore, the inspecting apparatus is located on the same floor as that of an automatic winder from which fluff scatters. This gives rise to a problem in that the fluff tends to enter the box, and the fluff becomes adhered to a slit of a projector, a lens of a camera and the like to degrade the inspection accuracy.

OBJECT AND SUMMARY OF THE INVENTION

A first object of the present invention is to provide a package inspecting apparatus which can effectively carry out yarn end processing, winding-form inspection and weight inspection of packages.

A second object of the present invention is to provide a package inspecting apparatus which can prevent entry of fluff into a box and can maintain the inspection accuracy constant.

A third object of the present invention is to provide an inspection apparatus which can discriminate and inspect off lease winding which involves a problem in quality of package and an overlapping of ribbons which involves no problem in unleasing.

For achieving the first object, a package inspecting apparatus according to the present invention comprises a yarn end processing section for exerting suction air on the surfaces of packages while rotating trays on a running passage for trays on which packages are fitted, a package inspecting section in which a plurality of optical type package winding-form inspecting devices are received in a dark room, and a weighing section provided with a weight measuring unit, said sections being arranged in series in said order and integrated.

The yarn end processing, winding-form inspection and weight inspection are carried out in order with the feeding of trays, and necessary processing and inspections are carried out as a series of steps within a single apparatus.

For achieving the second object, the present invention provides a package inspecting apparatus for carrying out an external-appearance inspection or the like with a package received into a box, characterized in that a blower is connected to said box to feed fresh air therein.

For achieving the third object, the inspecting apparatus according to tile present invention comprises a support device for rotatably supporting a package, a light source for irradiating a diametral direction of an end of the packaged rotated by said support device, a CCD line sensor for reading off lease winding of the package end and a reflecting light of a ribbon, a binary-coded circuit for binary-coding output information of the CCD line sensor resulting from the rotation of the package, a calculation circuit for calculating a bulge of a parabolic curve recognized via said binary-coded circuit, and a comparator for comparing said bulge with a predetermined value.

BRIEF DESCRIPTION OF THE DRAWINGS

FIG. 2 is a longitudinal sectional view of a yarn end processing section.

FIG. 3 is a top view showing a tray rotating mechanism.

DETAILED DESCRIPTION OF PREFERRED EMBODIMENTS

Figure 1:
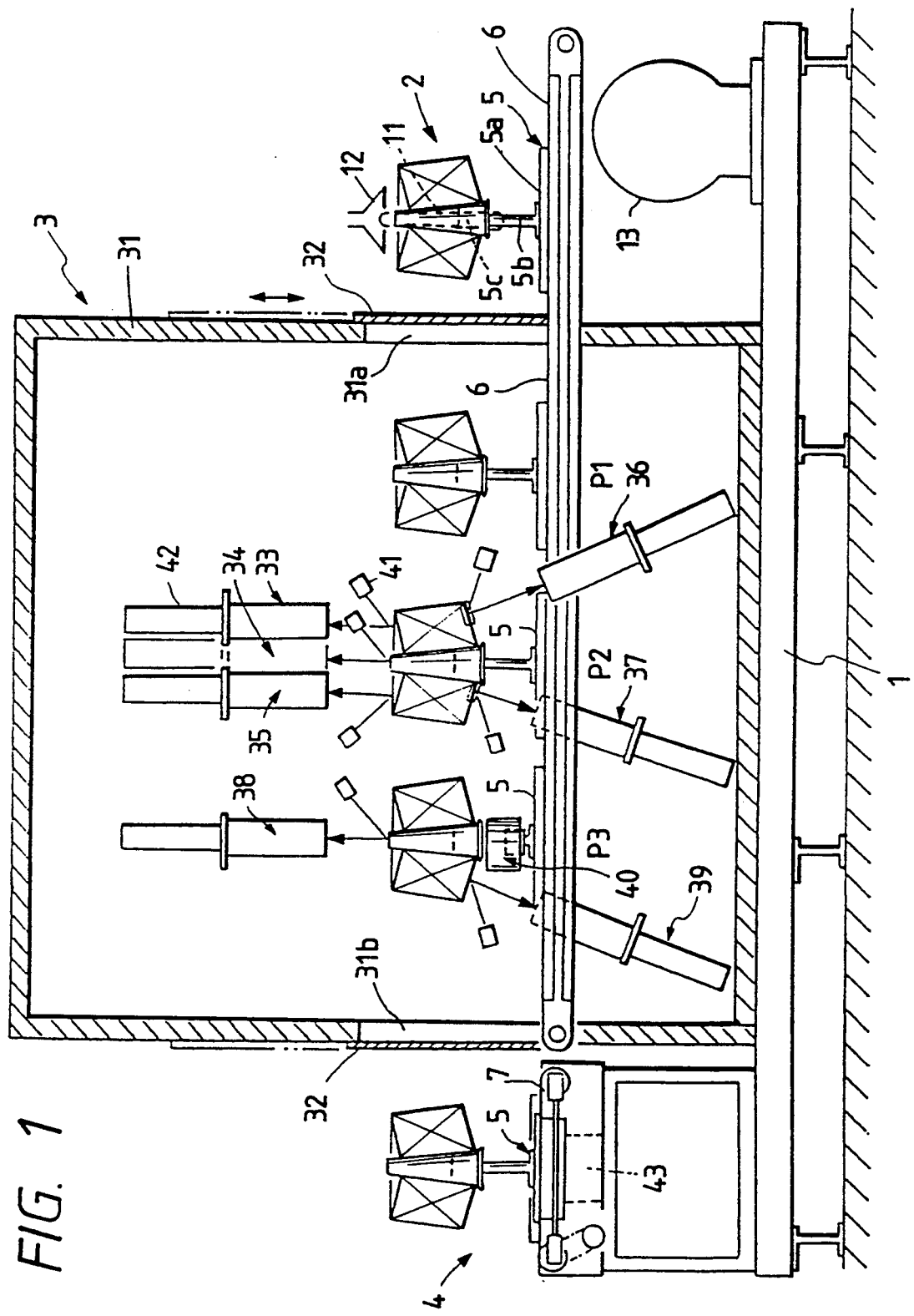
FIG. 1 is a cross-sectional view of a package inspecting apparatus according to the present invention.

Embodiments of the present invention will be described hereinafter with reference to the drawings. FIG. 1 is a cross-sectional view of a package inspecting apparatus according to the present invention.

In FIG. 1, the inspection apparatus has a yarn end processing section 2, a package inspecting section 3 and a weighing section 4 installed on a common base bed 1. A tray 5 having a package P fitted thereon consists of a disk 5a, a shaft 5b and a cone 5c, and supports the package P while being raised from the disk 5a. A conveyor for carrying the tray 5 consists of a first conveyor 6 common to the yarn end processing section 2 and the package inspecting section 3, and a second conveyor 7 singly provided on the weighing section 4.

The yarn end processing section 2 is provided with a suction mouth 11 for side and a suction mouth 12 for end, said mouths 11 and 12 being connected to a suction blower 13. As shown in FIG. 2, the suction mouth 12 sucks yarn waste stayed on the upper end of the package and yarn waste remained in a paper tube B, the suction mouth 12 being vertically movably supported by a cylinder 14. The dash-dotted contour lines indicate the withdrawal state, and when the tray 5 stops at a predetermined position, it moved down to the solid-line position to effect suction through a suction blower. The suction mouth 11 properly rewind a wound end and straightens slackness of a bunch winding. Therefore, the suction mouth 11 is operated while rotating the tray 5. The package P is formed rotated in an unwinding directin, and a wound end Y1 is sucked. The suction the wound end Y1 is detected by a sensor 15, and when the wound end Y1 is sucked in a predetermined amount, the package P is rotated in a winding direction so that proper winding about the outer periphery of the package P is obtained. With respect to a bunch winding 2, similar detection is made by a sensor 16 and rewinding is carried out. This suction mouth 11 has an arcuate hood 17 and can be moved forward and backward by a cylinder 18.

A mechanism for rotating the tray 5 at a predetermined position will be described with reference to FIG. 3. Along the first conveyor 6 are disposed a stopper 22 opened and closed by a solenoid 21, a positioning roller 24 urged by a spring 23, a driving roller 26 rotated by a motor 25 and a guide roller 27. When the positioning roller 24 is pushed open to feed the tray 5, it stops at the stopper 22 at the solid line position and assumes a predetermined position by the urging force of the positioning roller 24. The tray 5 is then rotated by the driving roller 26, and the pakcage is also rotated.

Returning to FIG. 1, the package inspecting section 3 will be described. A dark room 31 for covering the first conveyor 6 itself is formed, and an opening and closing door 32 is mounted on exists 31a and 31b of the dark room 31. A first position P1, a second position P2 and a third position P3 are provided in the moving direction on the first conveyor 6 within the dark room 31. A first position P1 is for standby, and a necessary optical type package winding-form inspecting device can be added according to the request of clients. The tray 5 at the second and third positions P2 and P3 can be rotated by the rotating mechanism similar to that shown in FIG. 3, and the winding-form inspection over the entire package is carried out. If inspection is made separately of the second and third positions P2 and P3 as described above, mutual interference caused by concentration of many optical type package winding-form inspecting devices on one place is avoided.

On the upper end of the package at the second position P2 are disposed a wrinkle inspecting device 33 for inspecting presence or absence of wrinkles, off lease winding inspecting device 34 for inspecting presence or absence of unleasing, and a bar winding inspecting device 35 for inspecting presence or absence of bar winding, and on the lower end of the package are disposed an outer periphery side off lease winding inspecting device 36 and an inner periphery side off lease winding inspecting device 37. Particularly, the unleasing on the large diameter side directly results in yarn breakage, and the outer periphery side and the inner periphery side are separately and positively detected. A different kind inspecting device 38 is disposed on the upper end of the package at the third position P3. Different kinds are detected according to a difference in color, that is, a difference in reflectance. Therefore, a separate installation is employed in order to avoid interference with others. On the lower end of the package are disposed a bar winding inspecting device 39 and a bunch winding inspecting device 40 for inspecting presence or absence of bunch winding. These inspecting devices are all composed of a light source 41 such as a halogen lamp and a sensor 42 such as a CCD camera. A reflecting light caused by off lease winding or the like is signal-processed to inspect presence or absence.

In the weighing section 4, a load cell 43 is disposed below the second conveyor 7 on which the tray 5 is placed, and the weight of the entire tray 5 is applied to the load cell 43 through a flexible conveyor. That is, when the weight of the tray 5 is subtracted, the weight of the package itself can be measured. In case of an unexpectedly large package, a trouble occurs in the packing step, and therefore, it is detected in advance.

Figure 4:
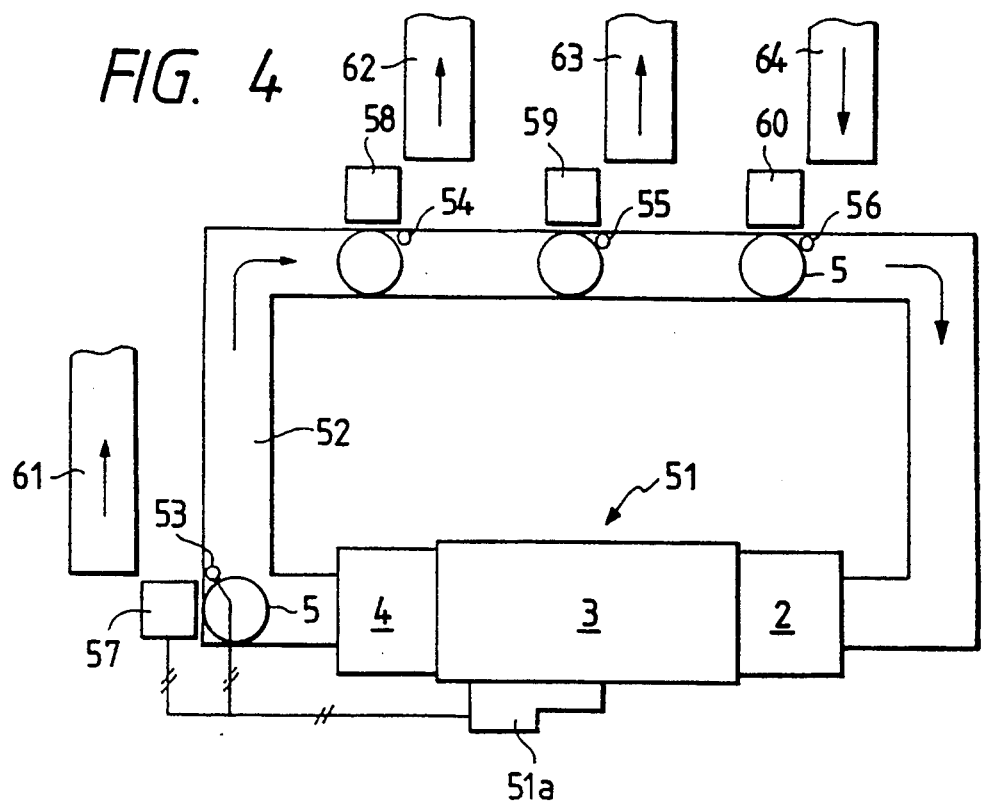
FIG. 4 is a view showing an inspection system using the inspecting apparatus according to the present invention.

In the aforementioned package inspecting apparatus, necessary inspections are completed before the package P fitted on the tray 5 is carried by the first and second conveyors 6 and 7. One example of an inspection system with such a package inspection apparatus incorporated therein will be described with reference to FIG. 4. In FIG. 4, reference numeral 51 designates a package inspection device; 52, a tray circulating conveyor; 53 to 56, stoppers; 57 to 60, transfer devices; 61 to 64, conveyors. A package prior to inspection on the conveyor 64 is fitted on the tray 5 stopped by the stopper 56 by the transfer device 60. All the necessary inspections are completed by the package inspection device 51. When a defective product occurs, the inspection result is inputted into the stopper 53 from a controller 51a, and the product is transferred to the conveyor 61 by the transfer device 57. Normal packages are stopped by the stoppers 54 and 55 and transferred to the conveyors 62 and 63 by the transfer devices 58 and 59. It is to be noted that the tray 5 itself is circulated for use. When the package inspection apparatus 51 is integrally configured, it can be simply incorporated into various systems.

The package inspecting apparatus according to the present invention comprises a yarn end processing section for exerting suction air on the surfaces of packages while rotating trays on a running passage for trays on which packages are fitted, a package inspecting section in which a plurality of optical type package winding-form inspecting devices are received in a dark room, and a weighing section provided with a weight measuring unit, said sections being arranged in series in said order and integrated. This apparatus is effective because necessary processing and inspections are carried out as a series of steps within a single apparatus.

Figure 5:
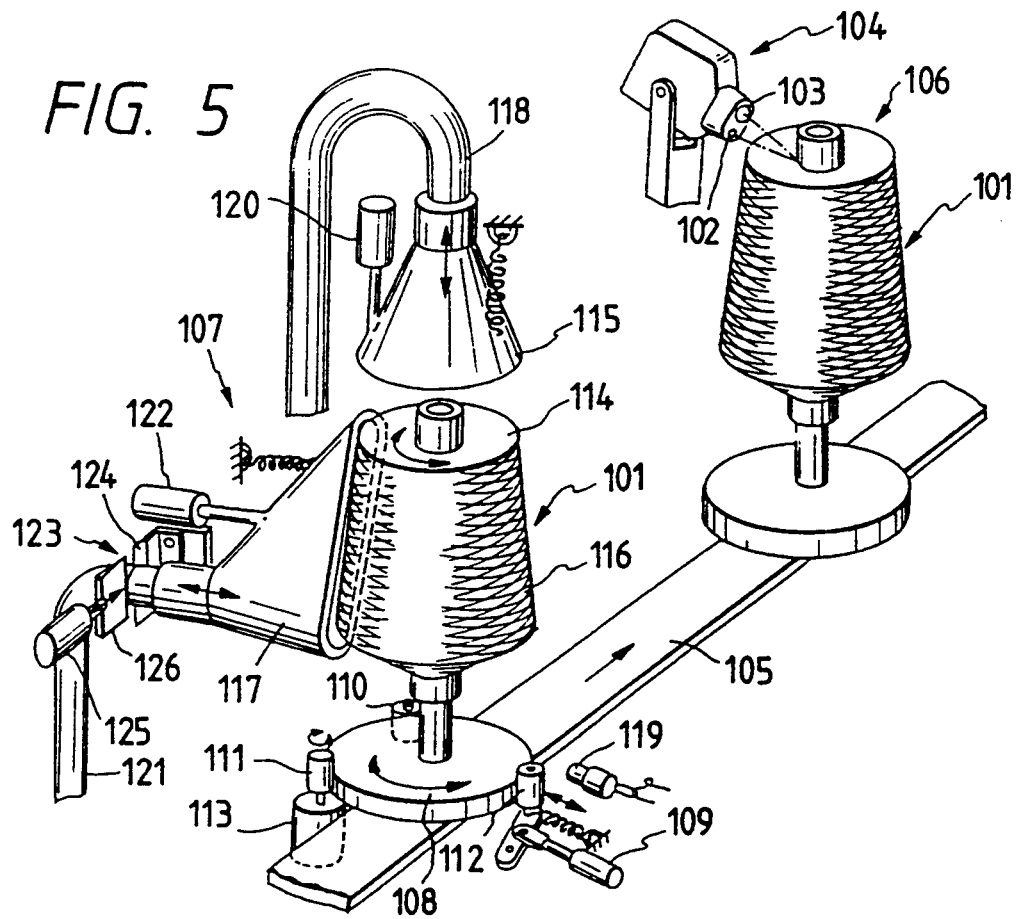
FIG. 5 is a perspective view of an embodiment according to the present invention.

Another embodiment of the yarn end processing section 2 is shown in FIG. 5. Signals from a light source 102 for irradiating a surface of a yarn layer of a package 101 and an image sensor 104 provided with a light receiving section 103 for receiving light reflected at the surface of the yarn layer are inputted into a signal processing means not shown and compared with a standard value whereby a signal for discrimination of right or wrong of a package of whether failure in end in the package surface, wrinkles, bars and mixed counts occur is outputted. Defective packages are removed from a system of a normal conveyor 105.

On the line of tile conveyor 105, a yarn suction device 107 is provided at upstream of a package inspecting section 106. The yarn suction device 107 is provided with a moving roller 112 in which a tray 8 is pressed toward support rollers 110 and 111 by a cylinder 109 in order that the tray 108 on which the package 101 is stood upright is stopped temporarily at a predetermined position. The support roller 111 can be rotated in both normal and reverse directions by means of a motor 113, and the tray 108 is rotated in a suitable direction by the motor 113 in tile state where the tray 108 is held by these three rollers 110, 111 and 112.

In the yarn suction device 107, with respect to tile package 101 stopped at a predetermined position, an upper suction mouth 115 is arranged at a portion opposed to an upper end 114 thereof, and a side suction mouth 117 is arranged at a portion opposed to the surface 116 of the package. Tile upper suction mouth 115 can be vertically moved by a cylinder 120 with respect to an upper suction duct 118, and tile side suction mouth 117 can be horizontally moved by a cylinder with respect to a side suction duct 121. The side suction duct 121 is provided with a cutter 123. A movable blade 126 is moved by a cylinder 125 with respect to a fixed blade 124 so that a yarn end passing therethrough can be cut.

In the above-described apparatus, when the tray 108 carried on the belt conveyor 105 passes a position sensor 119 portion, the cylinder 109 is actuated by an output signal thereof to move the moving roller 112 toward the support rollers 112 and 111. The tray 108 is held between these rollers to stop carrier.

Subsequently, the cylinder 122 is actuated to move the side suction mouth 117 close to the surface 116 of tile package 101. Then, the motor 113 is reversed to rotate for about two revolutions in the direction opposite to the winding direction of the package 101 on which tile tray 108 is stood upright. Thereby, the yarn waste adherred to the package surface is sucked and removed, and the yarn end hung on the package surface 6 is sucked. The yarn end is sucked into the side suction duct 121 during the reversal of the package for about two revolutions. When the motor stops its rotation, the cylinder 125 is actuated so that the movable blade 126 is moved toward the fixed blade 124 to cut tile yarn end sucked ill the side suction duct 121 at a predetermined length portion thereof. After cutting, the cylinder 125 is placed in non-operating state to return the movable blade 123 to its original position. At the same time, the cylinder 120 is actuated to move down the upper suction mouth 115 so as to be close to the upper end 114 of the package 101 to suck the yarn waste adherred to the upper end.

Next, the motor 113 is normally driven to wind the cut yarn end about the package end. The number of revolutions required to terminate winding differs with the position of the cutter 123. With about one normal revolution, all the yarn end are wound about the package side. Upon termination of these yarn waste suction and yarn end processing, the cylinder 122 is placed in non-operating state to withdraw the side suction mouth 117 to its original position, and the cylinder 120 is also placed in non-operating state to move upward the upper suction mouth 115. Finally, the cylinder 109 is placed in non-operating state to withdraw the moving roller 112 to its original position and release its stoppage caused by holding the tray 108. The tray is carried by the belt conveyor 105 to send it to the package inspection section 106 provided adjacent thereto.

In the package inspecting section 106, the aforementioned external appearance inspection is conducted by the image sensor 141, and the measurement of weight of the package is carried out in the weighing section in the succeeding step.

This embodiment of the present invention has the construction as described above and operates as described above. The yarn waste adhered to the surface of the package is sucked and removed, and an erroneous operation caused by adherence of yarn waste can be eliminated in the package inspecting section to improve the reliability of the package inspecting apparatus.

Hereinafter, an embodiment, in which a blower is connected to a box to feed fresh air therein in a package inspecting apparatus for carrying out an external-appearance inspection or the like with a package received into a box, will be illustrated. According to this embodiment, fresh air is fed into the box of the inspection apparatus by the blower so that the interior of the box is under positive pressure than the outside the box. It is therefore possible to prevent entry of fluff scattering outside the box into the box. Accordingly, since the fluff is not adhered to the inspection device, the inspection accuracy can be maintained constant.

Figure 6:
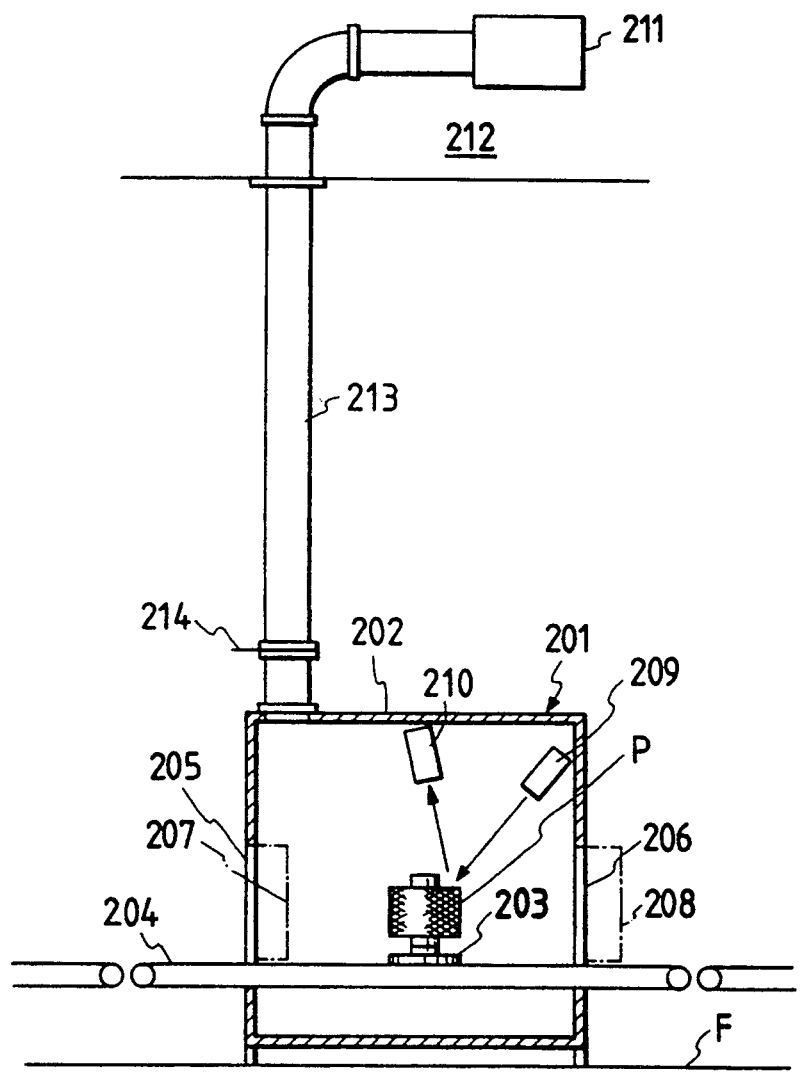
FIG. 6 is a sectional view showing another embodiment of the package inspecting apparatus according to the present invention.

In FIG. 6, reference numeral 201 designates an inspecting apparatus for carrying out an external appearance inspection or the like for a package P. The apparatus is installed on the same floor F as that of an automatic winder not shown, and packages P produced from the automatic winder thereto.

The inspecting apparatus 201 is provided with a box 202 which serves as a dark room when the package P is received for inspection. A conveyor 204 is installed on the box 202 so as to extend therethrough in a state where the package P is placed on a tray 203. The box 202 is formed in a front wall and a rear wall with an inlet 205 and an outlet 206 for packages, these inlet 205 and outlet 206 being provided with French doors 207 and 208 which are automatically opened and closed when the package P passes therethrough.

The box 202 is interiorly provided with a projector 209 for projecting light on a yarn layer of the package P, a camera 210 for receiving a reflecting light therefrom, and inspecting devices such as a weighing unit (not shown) for measuring a weight of the package P.

A blower 211 is connected to the box 202 so as to feed fresh air into the box 202 to maintain the interior of the box 202 positive pressure than the outside the box 202. The blower 211 is installed in a place separately from the floor F, for example, in a room 212 in the ceiling so that fresh air can be fed, said blower 211 and said box 202 being connected by a blowing pipe 213. Reference numeral 214 designates an air quantity adjusting shutter provided in the blowing pipe 213.

In the above-described structure, fresh air is fed into the box 202 of tile inspecting apparatus 201 by the blower 211, and extra air is discharged outside the box 202 through clearances of the doors 207 and 208. Accordingly, the interior of the box 202 is maintained at pressure slightly higher than the outside the box 202, that is, positive pressure, and the fluff scattering outside the box 202 will not enter the box 202 to enable prevention of adherence of fluff to the inspecting device to maintain the inspection accuracy constant.

According to this embodiment, fresh air is fed into the box of the inspecting apparatus, and the interior of the box is under positive pressure than tile outside tile box. It is therefore possible to prevent the fluff scattering outside the box from entering the box, and the inspecting accuracy can be maintained constant.

The cone-like packages or the like produced by the automatic winder are subjected to various inspections prior to shipment. As one of such inspections, there is an inspection for inspecting presence or absence of off lease winding in the end of the package. The off lease winding means that a yarn is externally deviated and wound in the end of the package. This tends to occur due to inaccuracy of traverse and large fluctuation of tension resulting from the traverse. The off lease winding produced in the end on the small diameter side of the cone-like package practically poses no problem but the off lease winding produced in the end on the large diameter side forms one of causes of yarn cutting when a package is released. The off lease winding package is defective.

Figure 10A:
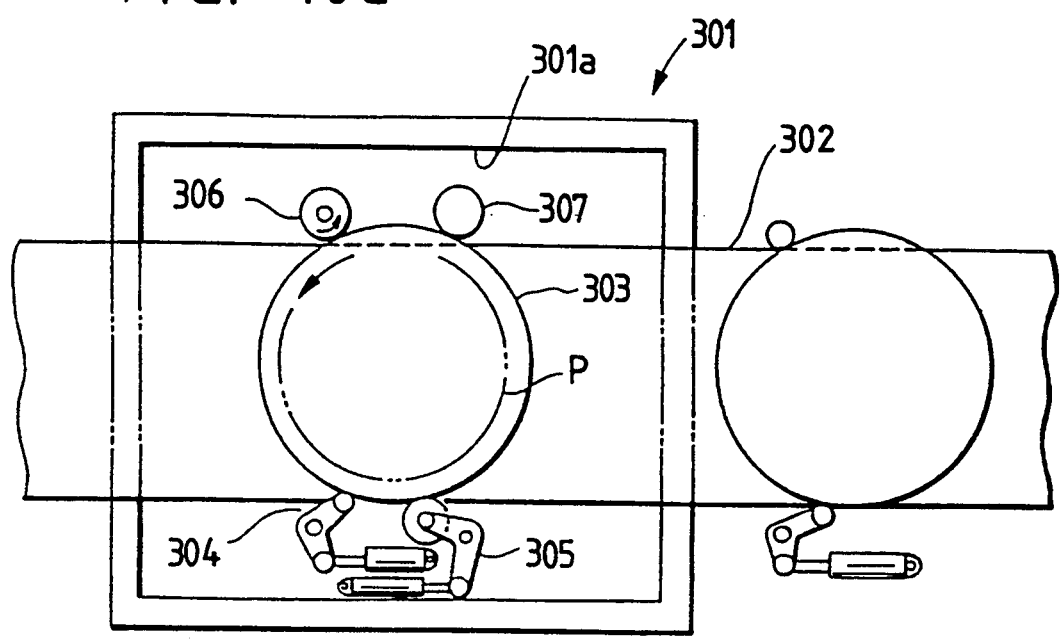
FIGS. 10a and 10b are a view of the entire inspecting apparatus.
Figure 10B:
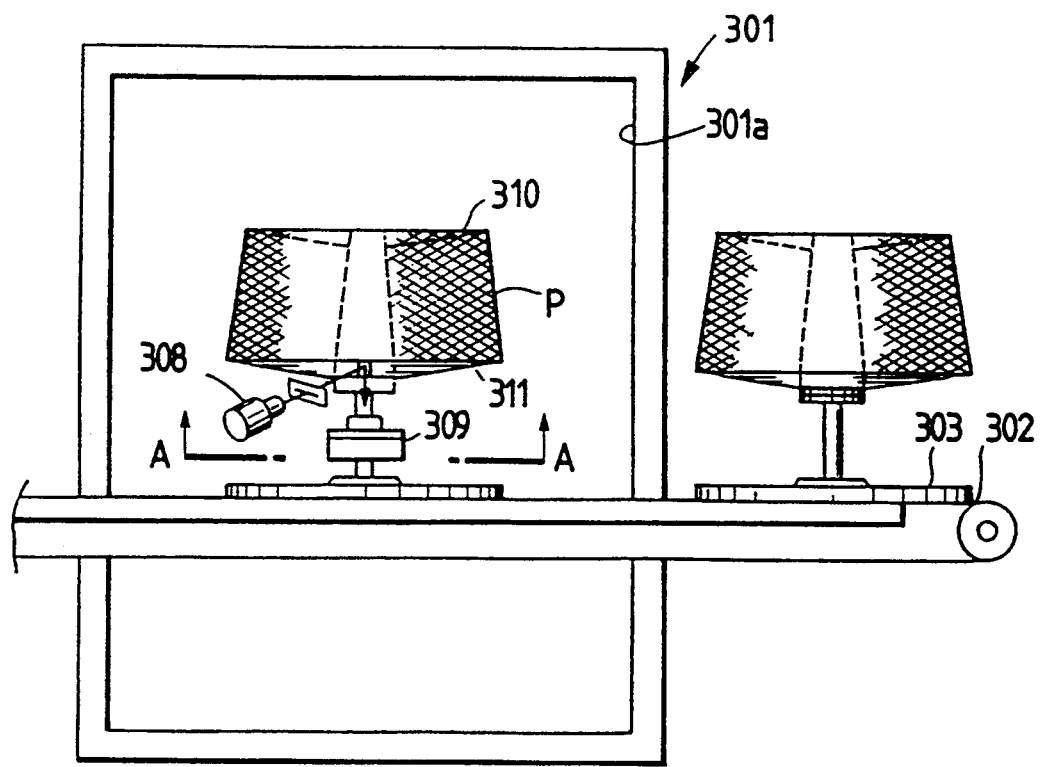

A conventional example of the inspecting apparatus in connection with the off lease winding will be described with reference to FIGS. 10 and 11. FIG. 10a is a top view of the inspecting apparatus, and FIG. 10b is a side view of the inspecting apparatus. In FIG. 10a, an inspection apparatus 301 is disposed in the middle of a conveyor 302. A package P is inserted in the state where it is raised by a tray 303 and is taken into the inspection apparatus 301 together with the tray 303. The interior of the inspecting apparatus 301 serves as a dark room 301a and is provided with a stopper 304 opened and closed by a solenoid or the like, a positioning roller 305 energized by a solenoid or the like, a driving roller 306 and a guide roller 307, along the conveyor 302. The tray 303 at a predetermined position is rotated by the driving roller 306, and the package P also rotates. That is, the tray 303, the driving roller 306 and the like constitute a support device for rotatably supporting the package P.

As shown in FIG. 10b, the dark room a is interiorly provided at upper and lower portions with a light source 308 such as a halogen lamp and a CCD line sensor 309 such as a CCD camera. These elements inspect presence or absence of off lease winding of the end on the large diameter side of the package P wich particularly poses a problem.

Figure 11:
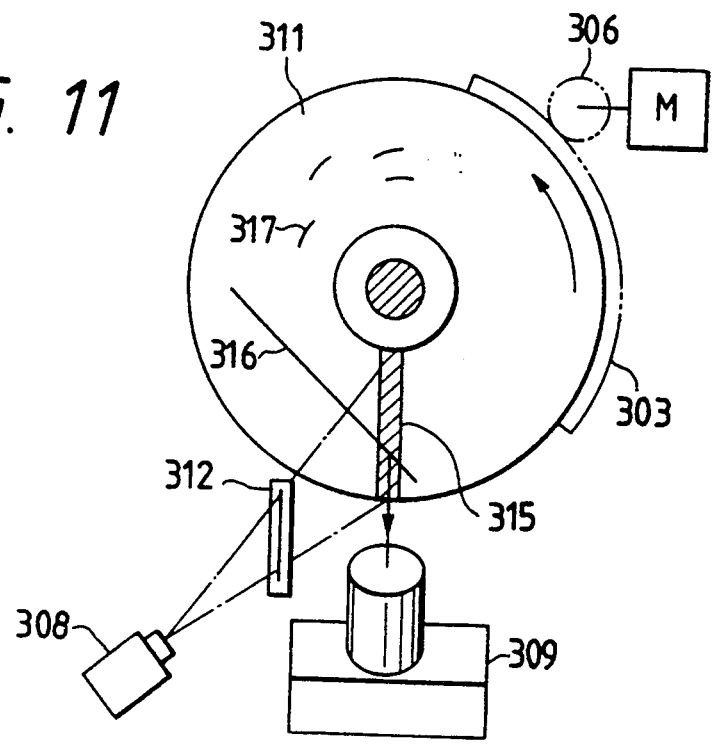
FIG. 11 is a view showing essential parts of a conventional inspecting apparatus.

Referring to FIG. 11 which is a sectional view taken on A—A of FIG. 10b, the detail of the off lease winding inspection by the light source 308 and the CCD line sensor 309 will be described. Reference numeral 312 designates a slit for forming an irradiation light by the light source 308 into a rectangle in a diametral direction of the package P; 303, a tray; and 306, a driving roller. The light source 308 and the CCD line sensor 309 are installed at a position within approximately 45° C. in a plane angle. An irradiation portion 315 indicated by the oblique line is formed on the end 311 on the large diameter side of the package P by the light source 308 and the slit 312, an the reflecting light at the off lease winding 316 is incident upon the CCD line sensor 309. The magnitude of the incident light specifies the portion of the off lease winding 316. A sensor having high resolution is required to read the magnitude of minute incident light, for which is used a CCD line sensor 309 in which 2048-bit solid image pickup elements are arranged in series. There are present a number of ribbons 317 (in which yarns at turnback portions of the traverse are overlaid to form an arcuate raised portion, which does not greatly influence on the,. quality of packages) in the end 311 on the large diameter side. A reflecting light is generated even by the ribbon 317. However, as shown, the ribbon 317 is shorter than the off lease winding 316. Discrimination can be made according to the length of the reflecting portion, that is, the extent of the rotational angle of the package P. If the rotational angle of the reflecting portion is large, the off lease winding hasd been judged.

Figure 8:
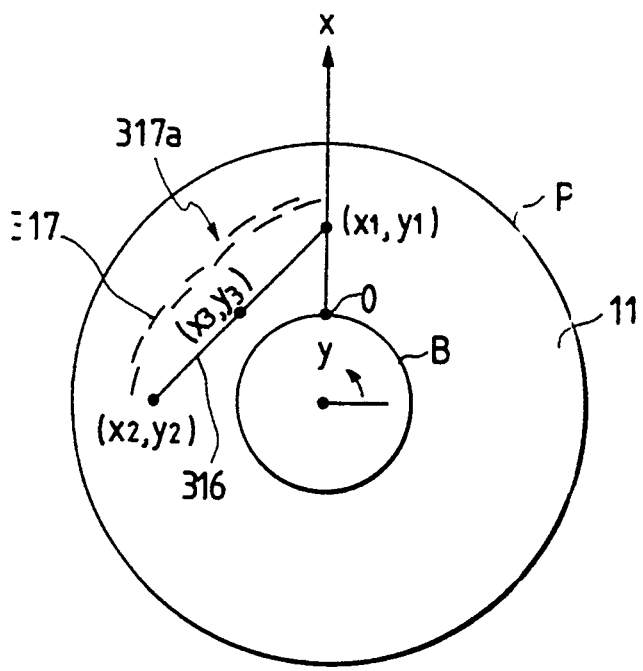
FIG. 8 is a status view of off lease winding in an end of a package and ribbon overlapping.

However, in the inspecting apparatus in which the large rotational angle of the reflecting portion is judged as the off lease winding, there is a problem in that as shown in FIG. 8, an overlapped ribbon 317a in which the ribbons 317 are accidentally continuously overlapped is sometimes judged to be an unleasing. Therefore, since a package having no problem in quality is judged to be abnormal, it is necessary to finally make reassurance by human's eyes.

The inspecting apparatus according to this embodiment of the present invention comprises a support device for rotatably supporting a package, a light source for irradiating a diametral direction of an end of the packaged rotated by said support device, a CCD line sensor for reading off lease winding of the package end and a reflecting light of a ribbon, a binary-coded circuit for binary-coding output information of the CCD line sensor resulting from the rotation of the package, a calculation circuit for calculating a bulge of a parabolic curve recognized via said binary-coded circuit, and a comparator for comparing said bulge with a predetermined value.

When position information of off lease winding as well as position information of ribbon overlapping are binary-coded, they form a parabolic curve. A linear off lease winding forms a deep parabolic curve but a ribbon overlapping forms a shallow parabolic curve. Paying attention to a difference therebetween, the off lease winding is discriminated from the ribbon overlapping in view of a degree of a bulge of the parabolic curve.

Figure 7:
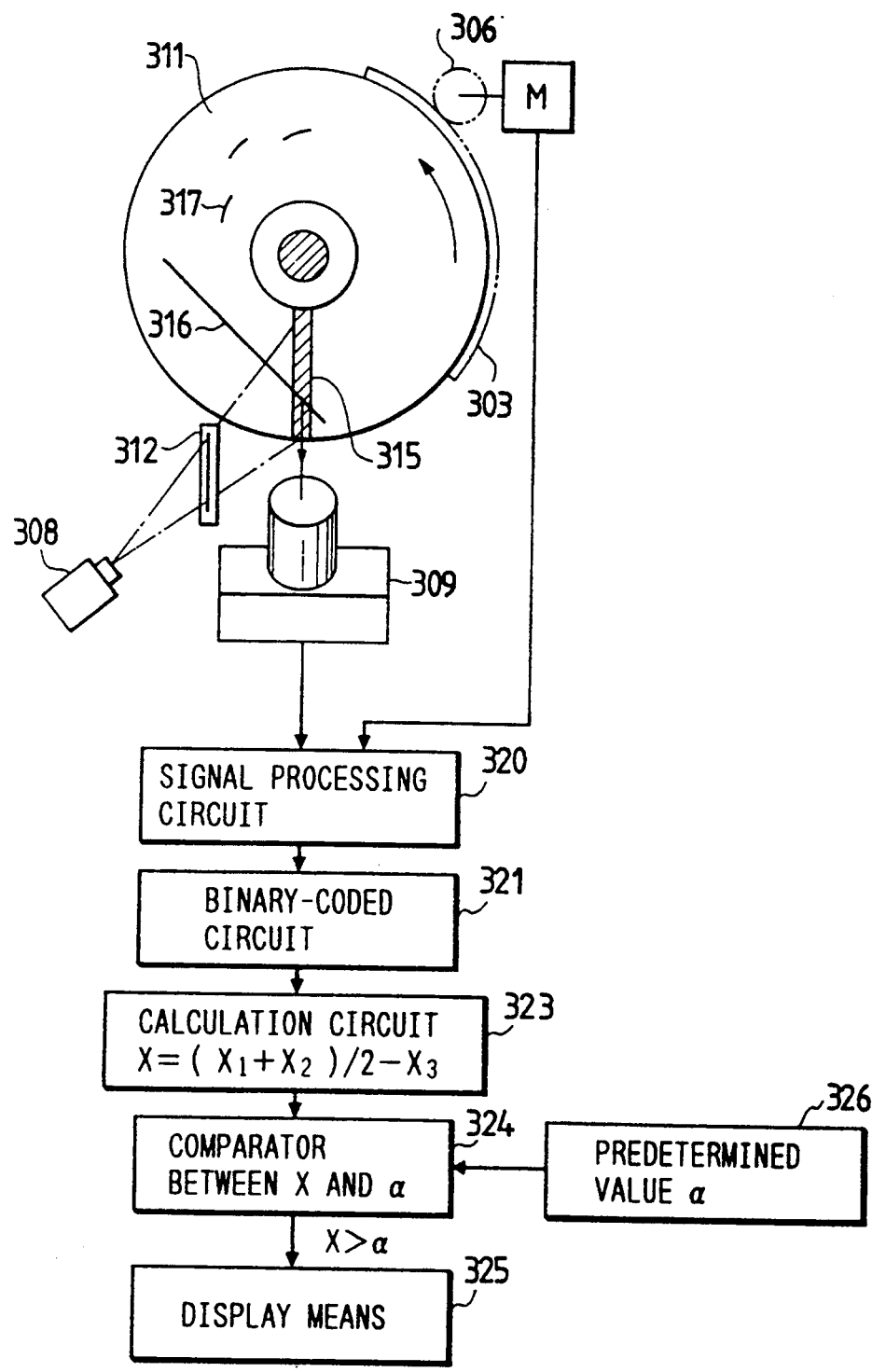
FIG. 7 is a view showing essential parts of still another embodiment of an inspecting apparatus according to the present invention.

FIG. 7 is a view showing essential parts of an inspecting apparatus according to the present invention. Parts different from those shown in FIG. 11 are parts in connection with processing of signals. Other parts are indicated by the same reference numerals and description thereof will be omitted.

In FIG. 7, a position in a diametral direction of a package of a reflecting light such as off lease winding is detected by the CCD line sensor 309, and a position of a circumferential angle of a shadow is detected by the number of revolutions of the driving motor 306. These position informations are processed by a signal processing circuit 320 and formed into plane position informations by a binary coded circuit 321. The off lease winding or the like can be recognized as a parabolic curve via the binary-coaded circuit 321 and subjected to computation by a calculation circuit 323 to calcualte a height X of the parabolic curve, and the extent of a bulge thereof is numerically processed. In a comparator circuit 324, the height X of the parabolic curve is compared with a predetermined value $\alpha$. If $X > \alpha$, off lease winding is judged, and abnormality of quality is displayed by display means 325. Reference numeral 326 denotes memory means for the predetermined value $\alpha$.

Figure 9:
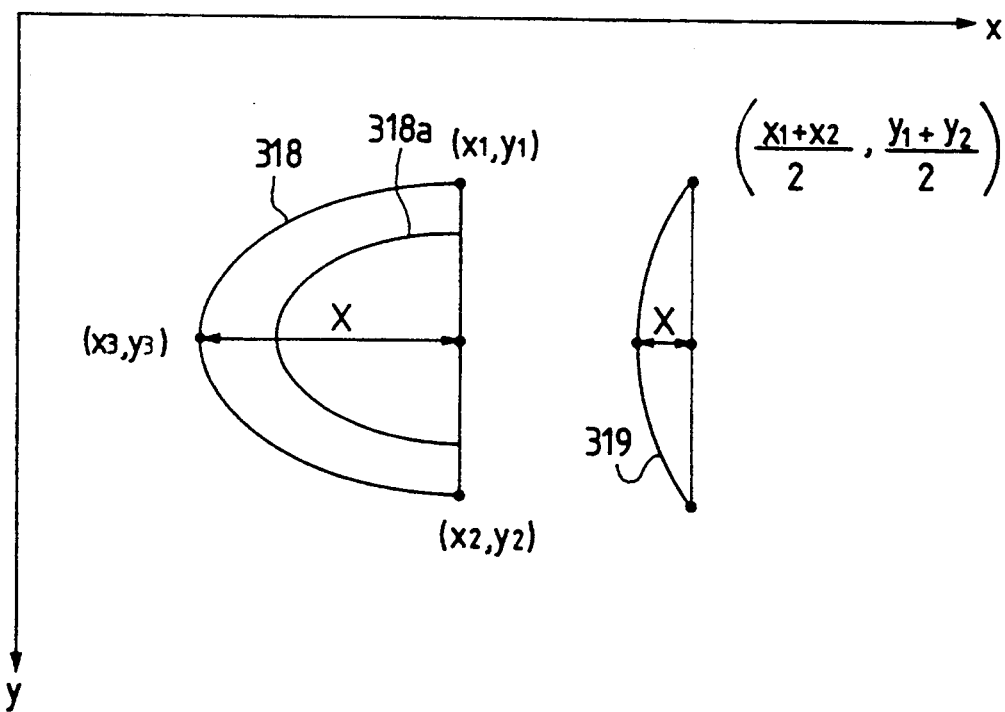
FIG. 9 is a graphic representation of parabolic curves of unleasing and ribbon overlapping.

The operation of the aforementioned inspecting apparatus will be described in detail hereinafter with reference to FIGS. 8 and 9. In FIG. 8, reference numeral 316 denotes off lease winding which is linear. Reference numeral 317a denotes a ribbon overlapping, which is arcuate. The diametral direction of the package P is the axis x with the bobbin B side to be zero, and the rotational angle of the package P is the axis y. In FIG. 9, in the off lease winding 316, the start point is $(x_1, y_1)$, the terminal is $(x_2, y_2)$, and the middle point is $(x_3, y_3)$. Since the middle point is closest to the bobbin B, the locus thereof is a deep parabolic curve 318. The height X of the parabolic curve 318 can be calculated by $X=(x_1+x_2)/2-x_3$, and a typical parabolic curve having a bulge has a considerable height X. On the other hand, the ribbon overlapping 317a in FIG. 8 is arcuate, and less fluctuation of the value x occurs. A crushed parabolic curve 319 as shown in FIG. 9 results. When the length of off lease winding is short, a small similar figure as in a parabolic curve 318a results but an extremely small off lease winding is not present. The parabolic curve 318a has a height to some extent. On the other hand, even if the arcuate ribbon overlapping is long, the height of the parabolic curve 319 is limited. Therefore, an experimental predetermined value $\alpha$ is set, and one in which the height X is larger than the predetermined value $\alpha$ is judged to be off lease winding, which is discriminated from the ribbon overlapping.

The inspecting apparatus according to this embodiment of the present invention comprises a binary-coded circuit for binary-coding output information of the CCD line sensor resulting from the rotation of the package, a calculation circuit for calculating a bulge of a parabolic curve recognized via said binary-coded circuit, and a comparator for comparing said bulge with a predetermined value. Paying attention to a difference between that a linear off lease winding is a deep parabolic curve and that a ribbon overlapping is a shallow parabolic curve, the off lease winding is discriminated from the ribbon overlapping according to the extent of a bulge of the parbolic curve. Therefore, off lease winding involving a problem in quality of package is discriminated from that involves no problem and detected.

Another embodiment will be described hereinafter.

Figure 15:
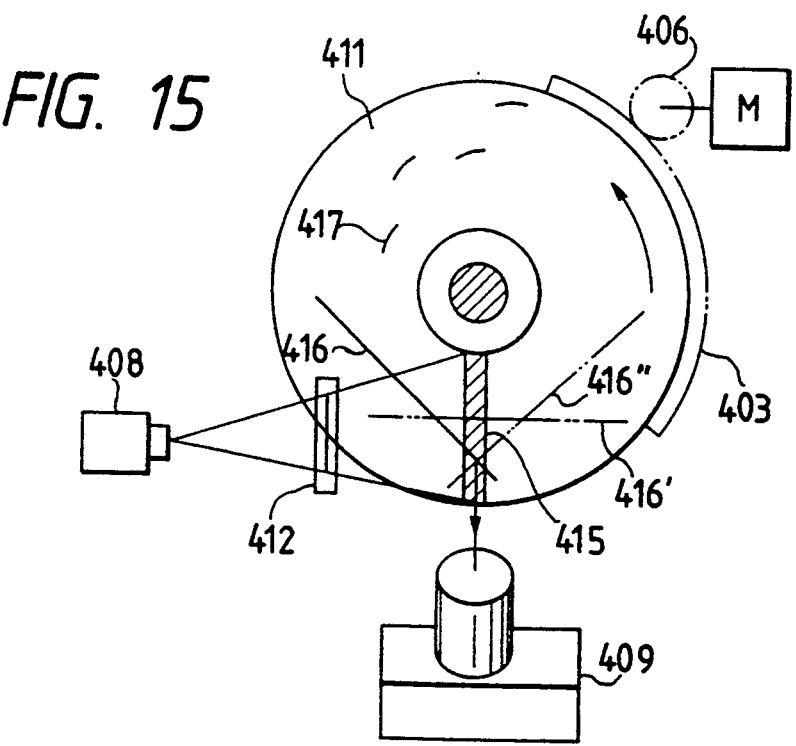
FIG. 15 is a view showing essential parts of a conventional inspecting apparatus.
Figure 13:
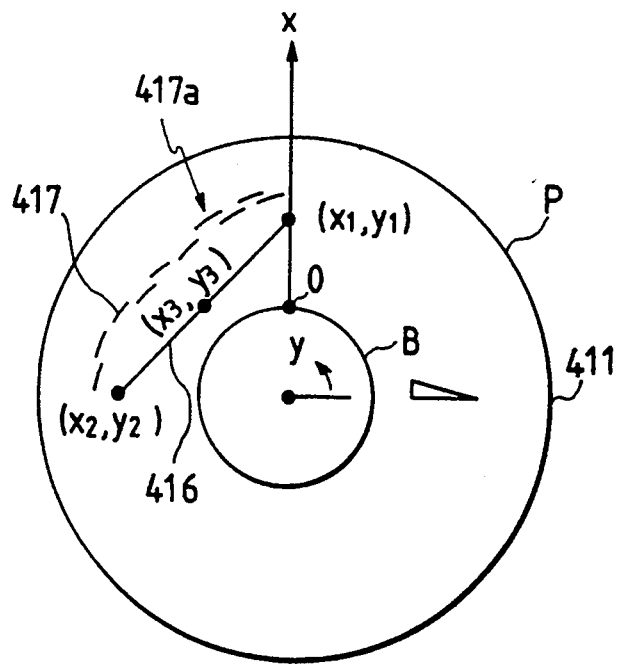
FIG. 13 is a status view of off lease winding of an end of a package and ribbon overlapping.

Tile prior art has a problem in that a ribbon overlapping 417a in which ribbons 417 are accidentally continuously overlapped as shown in FIG. 13 is sometimes judged to be off lease winding. Further, as shown in FIG. 15, when a light source 408 and a CCD line sensor 409 are installed at a position at which plane angle is approximately 90° the package rotates counterclockwise, and when unleasing 416' parallel with the light source 408 results, no reflecting light occurs. When the package further rotates counterclockwise, light reflects on the opposite side and conversely a thin shadow is detected. Therefore, about half of the off lease winding 416 is clear but the remaining half is unclear. That is, there was also a problem in that the length of the off lease winding 416 is sometimes judged to be short according to the extent of the installation angle of the light source 408 and the CCD line sensor 409.

An inspecting apparatus capable of adequately judging the case where about half of unleasing is unclear will be described hereinafter.

This embodiment of the present invention provides an inspecting apparatus comprising a support device for rotatably supporting a package, a light source for irradiating a diametral direction of an end of a package rotated by said support device, a CCD line sensor for reading off lease winding of an end of a package and a reflecting light of a ribbon, and a binary-coded circuit for binary-coding position information of the CCD line sensor resulting from the rotation of the package, a calculation circuit for calculating the ratio of height to width of a semiparabolic curve recognized via said binary-coded circuit, and a comparator for comparing the value of said ratio with a predetermined value.

When position information of off lease winding as well as position information of ribbon overlapping are binary-coded, a parabolic curve results but a linear off lease winding is a deep parabolic curve and the ribbon overlapping is a shallow parabolic curve. Paying attention to a difference therebetween and paying attention to the fact that at least half parabolic curve is clear, the off lease winding is discriminated from the ribbon overlapping according to the ratio of height to width of the half parabolic curve.

Figure 12:
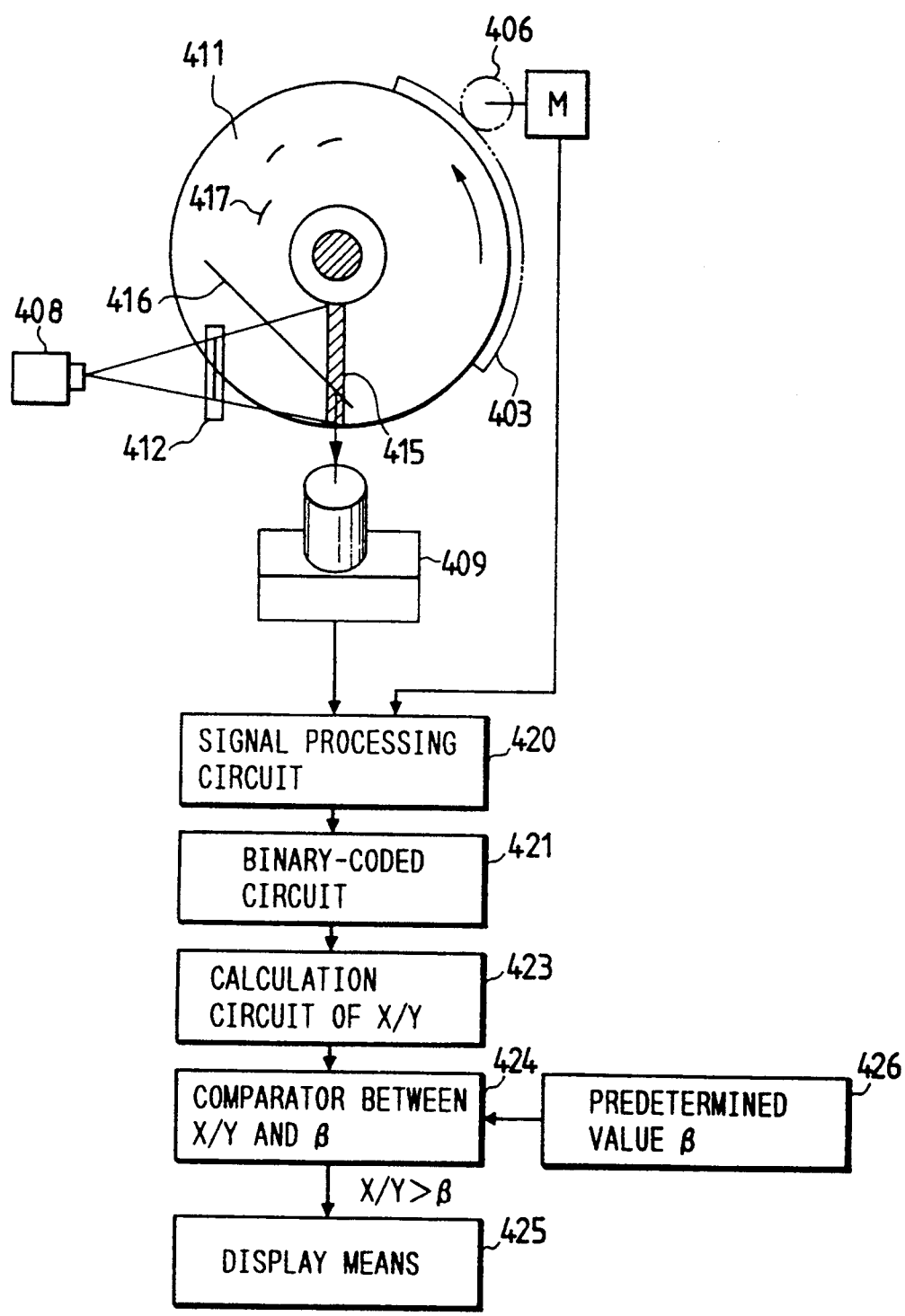
FIG. 12 is a view showing essential parts of further embodiment of an inspecting apparatus according to the present invention.

FIG. 12 is a view showing essential parts of an inspecting apparatus according to the present invention.

In FIG. 12, a position in a diametral direction of a package is detected by a CCD line sensor 49, and a position in a direction of circumferential angle is determined by the number of revolutions of a driving motor 406. These position informations are processed by a signal processing circuit 420 and formed into plane position informations by a binary-coded circuit 421. A parabolic curve recognized via the binary-coded circuit 422 is arithmetically processed by a calculation circuit 423 to calculate X/Y which is the ratio between height X and width Y of the parabolic curve. The X/Y of the parabolic curve is compared with a predetermined value $\beta$ by a comparator 424. If $X/Y > \beta$, unleasing is judged, and abnormal quality is displayed by display means 425. Reference numeral 426 denotes memory means for the predetermined value $\beta$.

Figure 14:
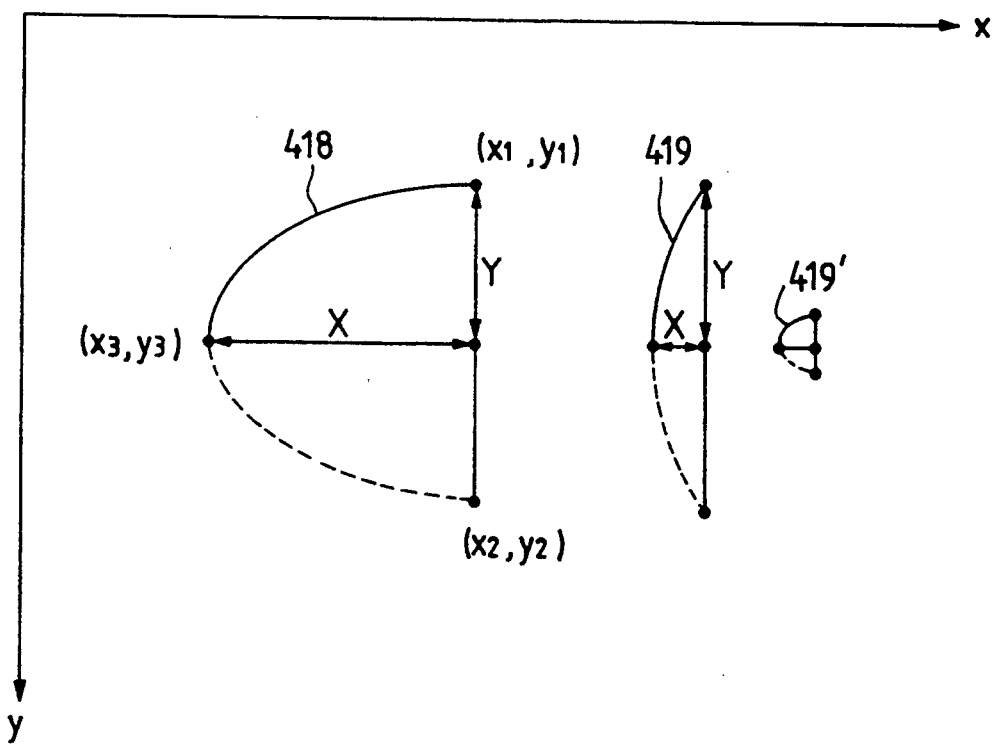
FIG. 14 is a graphic representation of parabolic curves of unleasing and ribbin overlapping.

In the following, the aforementioned inspecting apparatus will be described in detail with reference to FIGS. 13 and 14. In FIG. 13, reference numeral 416 denotes off lease winding which is linear. Reference numeral 417a denote ribbon overlapping which is arcuate. The diametral direction of the package P is the axis x with the bobbin B side to be zero, and the rotational angle of the package P is the axis y. In FIG. 14, in the off lease winding, the start point is $(x_1, y_1)$, the terminal point is $(x_2, y_2)$, and the middle point is $(x_3, y_3)$. Since the middle point is closest to the bobbin B, the locus thereof is a typical parabolic curve 418. However, when the light source and the CCD line sensor are installed at a position of 90° in plane angle, the reflecting light of the off lease winding from the start point $(x_1, y_1)$ to the middle point $(x_3, y_3)$ is clear but the reflecting light from the middle point $(x_3, y_3)$ to the terminal point $(x_2, y_2)$ is conversely thin shadow which is unclear. As the result, half of the parabolic curve 418 in FIG. 14 is clear while the remaining half is unclear, which is sometimes difficult to be detected. However, the height X and the width Y of the half parabolic curve 418 in the clear portion can be calculated from the start point $(x_1, y_1)$ to the middle point $(x_3, y_3)$. If the typical parabolic curve results, the ratio of X/Y is a certain value. On the other hand, the ribbon overlapping 417a in FIG. 13 is arcuate, and less fluctuation of the value x occurs. The crushed parabolic curve 419 as shown in FIG. 14 results, and the ratio X/Y between the height X and the width Y is small. Accordingly, by comparing at least the ratio X/Y between the height X and the width Y of the half parabolic curve, the off lease winding can be discriminated from the ribbon overlapping. Thus, the experimental predetermined value $\beta$ is set, and in case where the ratio X/y is greater than the predetermined value $\beta$, the off lease winding is judged, which is discriminated from the ribbon overlapping.

In FIG. 14, one ribbon is sometimes detected as a small half parabolic curve 419'. In a package in which when the ratio X/Y is accidentally large, the off lease winding is possibly recognized, the condition in which the height X or width Y is larger than a predetermined value γ is additionally added, and unleasing can be detected further positively.

The inspecting apparatus according to the present invention comprises a binary-coded circuit for binary-coding position information of a CCD line sensor resulting from the rotation of a package, a calculation circuit for calculating a ratio of height to width of a half parabolic curve recognized via said binary-coded circuit and a comparator for comparing the value of said ratio with a predetermined value. Paying attention to a difference between that a linear off lease winding is a deep parabolic curve and that a ribbon overlapping is a shallow parabolic curve and paying attention to that at least half parabolic curve is clear, the off lease winding is discriminated from the ribbon overlapping according to the ratio of height to width of the parabolic curve. It is therefore possible to discriminate and detect off lease winding involving a problem in quality of package and a ribbon involving no problem.

What is claimed is:

1. An apparatus for readying and inspecting a package having a yarn end, the apparatus comprising:
   an inspection station, the inspection station comprising: projection means for irradiating a surface of the package, light receiving means for receiving light reflected from the surface of the package, and
   a processing station provided upstream of the inspection station, the processing station comprising:
   suction means for applying a suction force to the surface of the package,
   means for rotating the package in a first direction whereby the yarn end is released into the suction means,
   means for cutting the yarn end released into the suction means to a predetermined length, and
   means for rotating the package in a second direction whereby the cut yarn end is wound around the surface of the package prior to delivery of the package to the inspection station.

2. An apparatus for readying and inspecting a package having a yarn end, the apparatus comprising:
   an inspection station, and
   a processing station provided upstream of the inspection station, the processing station comprising:
   suction means for applying a suction force to the surface of the package,
   means for rotating the package in a first direction whereby the yarn end is released into the suction means,
   means for cutting the yarn end released into the suction means to a predetermined length, and
   means for rotating the package in a second direction whereby the cut yarn end is wound around the surface of the package prior to delivery of the package to the inspection station.

* * * * *